United States Patent
Pilz et al.

(10) Patent No.: US 9,730,450 B2
(45) Date of Patent: *Aug. 15, 2017

(54) USE OF ISOSORBIDE MONOESTERS AS ANTIMICROBIAL ACTIVE SUBSTANCES

(75) Inventors: Maurice Frederic Pilz, Frankfurt am Main (DE); Peter Klug, Grobostheim (DE); Franz-Xaver Scherl, Burgkirchen (DE); Joerg Grohmann, Munich (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/237,039

(22) PCT Filed: Jul. 31, 2012

(86) PCT No.: PCT/EP2012/003246
§ 371 (c)(1),
(2), (4) Date: Jul. 9, 2014

(87) PCT Pub. No.: WO2013/017257
PCT Pub. Date: Feb. 7, 2013

(65) Prior Publication Data
US 2014/0315996 A1    Oct. 23, 2014

(30) Foreign Application Priority Data
Aug. 4, 2011  (DE) .................. 10 2011 109 435

(51) Int. Cl.
| | | |
|---|---|---|
| *A61K 31/34* | (2006.01) | |
| *A01N 43/90* | (2006.01) | |
| *A61K 45/06* | (2006.01) | |
| *A61K 31/047* | (2006.01) | |
| *A61K 31/341* | (2006.01) | |
| *A61K 8/49* | (2006.01) | |
| *A61Q 17/00* | (2006.01) | |
| *A61Q 19/00* | (2006.01) | |

(52) U.S. Cl.
CPC .......... *A01N 43/90* (2013.01); *A61K 8/4973* (2013.01); *A61K 31/047* (2013.01); *A61K 31/34* (2013.01); *A61K 31/341* (2013.01); *A61K 45/06* (2013.01); *A61Q 17/005* (2013.01); *A61Q 19/007* (2013.01); *A61Q 19/00* (2013.01)

(58) Field of Classification Search
CPC .... A61K 31/34; A61K 8/4973; C07D 493/04; A01N 43/90
USPC .......... 549/429, 464; 514/461, 470
See application file for complete search history.

(56) References Cited

U.S. PATENT DOCUMENTS

| | | | |
|---|---|---|---|
| 3,331,742 A | 7/1967 | Babayan | |
| 4,637,930 A | 1/1987 | Konno et al. | |
| 4,711,775 A | 12/1987 | Dittmar et al. | |
| 4,847,088 A | 7/1989 | Blank | |
| 6,413,529 B1 | 7/2002 | Beerse et al. | |
| 8,642,525 B2 | 2/2014 | Herrwerth et al. | |
| 9,295,626 B2 * | 3/2016 | Pilz ................. | A01N 43/90 |
| 9,358,199 B2 * | 6/2016 | Pilz ................. | C09D 7/002 |
| 9,445,595 B2 * | 9/2016 | Pilz ................. | C11D 1/667 |
| 2005/0222276 A1 | 10/2005 | Schmaus et al. | |
| 2007/0178144 A1 | 8/2007 | Hameyer et al. | |
| 2008/0142023 A1 | 6/2008 | Schmid | |
| 2008/0312195 A1 | 12/2008 | Simsch et al. | |
| 2010/0113664 A1 | 5/2010 | Bradshaw et al. | |
| 2011/0104085 A1 | 5/2011 | Klug et al. | |
| 2011/0117036 A1 | 5/2011 | Chaudhuri et al. | |
| 2012/0035090 A1 | 2/2012 | Breffa et al. | |
| 2012/0100085 A1 | 4/2012 | Klug et al. | |
| 2012/0101135 A1 | 4/2012 | Klug et al. | |
| 2012/0116101 A1 | 5/2012 | Fuertes et al. | |
| 2014/0308224 A1 | 10/2014 | Pilz et al. | |
| 2014/0322151 A1 | 10/2014 | Fricke et al. | |
| 2014/0323564 A1 | 10/2014 | Pilz et al. | |

(Continued)

FOREIGN PATENT DOCUMENTS

| | | |
|---|---|---|
| CA | 1231046 | 1/1988 |
| DE | 3328372 | 3/1984 |

(Continued)

OTHER PUBLICATIONS

English-translation of International Preliminary Report on Patentability for PCT/EP2012/003246 dated Feb. 4, 2014.
International Search Report for PCT/EP2012/003246 dated Oct. 18, 2012.
Peter Stoss et al., "Regioselektive Acylierung von 1, 4:3, 6-Dianhydro-D-glucit," Synthesis, vol. 1987, No. 02, pp. 174-176, Jan. 1, 1987.
English-language Abstract of JP 8187070.

(Continued)

*Primary Examiner* — Golam M M Shameem
(74) *Attorney, Agent, or Firm* — Tod A. Waldrop

(57) ABSTRACT

The use of one or more compounds of the formula (I)

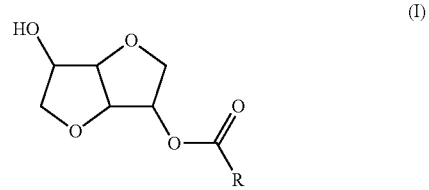

(I)

in which
R is a straight-chain or branched saturated alkyl group having 5 to 11 carbon atoms or a straight-chain or branched mono- or polyunsaturated alkenyl group having 5 to 11 carbon atoms
as antimicrobially active compound is described.
The use is preferably in cosmetic, dermatological or pharmaceutical compositions, in crop protection formulations, in washing or cleaning compositions or in paints or coatings.

15 Claims, No Drawings

(56) References Cited

U.S. PATENT DOCUMENTS

| | | |
|---|---|---|
| 2014/0329870 A1 | 11/2014 | Pilz et al. |
| 2014/0343171 A1 | 11/2014 | Pilz et al. |
| 2014/0348763 A1 | 11/2014 | Pilz et al. |
| 2014/0369943 A1 | 12/2014 | Pilz et al. |
| 2016/0000080 A1 | 1/2016 | Pilz et al. |

FOREIGN PATENT DOCUMENTS

| | | |
|---|---|---|
| DE | 2234009 | 12/1987 |
| DE | 10 2009 022 445 A1 | 12/2009 |
| DE | 10 2009 022 444 A1 | 1/2010 |
| EP | 1813251 | 8/2007 |
| EP | 1972330 | 9/2008 |
| EP | 2239315 | 10/2010 |
| JP | 59-175408 | 10/1984 |
| JP | H 01313408 | 12/1989 |
| JP | H 03168075 | 7/1991 |
| JP | 8187070 A | 7/1996 |
| JP | H 08173787 | 7/1996 |
| JP | H 09291016 | 11/1997 |
| JP | 2002541181 | 12/2002 |
| JP | 2003238396 | 8/2003 |
| JP | 2007203288 | 8/2007 |
| WO | WO 2006103338 | 10/2006 |
| WO | WO 2008155159 | 12/2008 |
| WO | 2010108738 A2 | 9/2010 |
| WO | 2010136121 A2 | 12/2010 |

OTHER PUBLICATIONS

Bach M. et al. Konservierungsmittel Und Ihre Praktische Anwendung in Kosmetischen Produkten, Sofw-Journal Seifen, Oele, Fette, Wachse, Verlag Fur Chemische Industrie, Angsburg, DE, vol. 116, No. 9, Jun. 13, 1990. pp. 942-7694, XP000134744.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database CA (Online), Chemical Abstracts Service, Columbus, Ohio (Aug. 14, 2008), Mori Toshiki; "Transparent cleaners comprising nonionic surfactants", XP002643078.
Database GNPD (Online), (Feb. 1999), Mintel; "Verzorgende Shampoo—Lang Harr", XP002662186.
English Abstract for JPH03168075, Jul. 19, 1991.
English Abstract for JPH09291016, Nov. 11, 1997.
Christian W. Klampfl et al., "Quantitative determination of UV filters in sunscreen lotions using microemulsion electrokinetic chromatography," J. Sep. Sci. Sep. 26, 2003, 1259-1262.
Database CA (Online) Chemical Abstracts Service, Feb. 24, 1985, "Cosmetics Containing Isosrbide Fatty Acid Diesters," Database Accession No. 1985:67233. English-language abstract of JP 59-175408.
Dubini Francesco et al., "In Vitro Antimycotic Activity and Nail Permeation Models of a Prioctone Olamine (Octopirox) Containing Transungual Water Soluble Technology," Arzneimittel Forschung. Drug Research, ECV Editio Cantor Verlag, vol. 55 No. 8, pp. 478-483, Jan. 1, 2005.
English-language Abstract of JP 8173787, Jul. 9, 1996.
English-language abstract of WO 2008/155159 A1, Dec. 24, 2008.
F.C. Kull et al., Applied Microbiology 1961, 9, 538.
Frieder W. Lichtenthaler, "Carbohydrates, Chapter 9: Carbohydrates as Organic Raw Materials," Ullmann's Encyclopedia of Industrial Chemistry, vol. 6, pp. 262-273, Jan. 1, 2003.
Giacometti, J. et al., "Process for Preparing Nonionic Surfactant Sorbitan Fatty Acid Esters with and without Previous Sorbitol Cyclization", J. of Agricultural and Food Chemistry, American Chemical Society, vol. 44, Jan. 1, 1996, pp. 3950-3954.
Seal, Kenneth J. et al., "Benzisothiazolinone and Methylisothiazolinone. New Preservative System," Cosmetic Technology, CEC, vol. 5, No. 1, pp. 47-52, Jan. 1, 2002.
Sorbitan Caprylate—the Preservative Boosting, Multifunctional Ingredient, Frederic Pilz, Cosmetic Science Technology, 2011, pp. 131-134.
A welcome side effect: How Velsan® SC (Sorbitan Caprylate) helps to reduce the concentration of classical preservatives, Fredric Pilz, et al., Household and Personal Care Today, Mar. 2010, pp. 22-24.
Velsan SC: Caprilato de sorbitán—Ingrediente multifuncional, conservante, hidrótropo y agente co-emulsionante, Fredric Pilz, et al., NCP 322, Nov.-Dec. 2011, pp. 15-19.
A preservative-free solution, Fredric Pilz, SPC, Oct. 2011.
Presentation by Fredric Pilz, at In-Cosmetics 2010 Paris, Apr. 5, 2010.
Presentation by Fredric Pilz, at SCS Formulate, Nov. 10, 2010.
Presentation by Fredric Pilz, at HPCI Koferenz—Asien, Dec. 17, 2010.
Presentation by Fredric Pilz, at In-Cosmetics 2011 Milano, Mar. 31, 2011.
Presentation by Fredric Pilz, at HPCI Koferenz—Turkey, Jun. 2, 2011.
International Preliminary Report on Patentability for PCT/EP2010/002919, dated Feb. 28, 2012.
International Search Report for PCT/EP2010/002919 mail date Nov. 15, 2011.
International Preliminary Report on Patentability for PCT/EP2010/002918, Dec. 2, 2011.
International Search Report for PCT/EP2010/002918 mail date Jun. 30, 2011.
English-Translation of International Preliminary Report on Patentability for PCT/EP2012/003248 dated Feb. 4, 2014.
International Search Report for PCT/EP2012/003248 dated Oct. 18, 2012.
English-Translation of International Preliminary Report on Patentability for PCT/EP2012/003247 dated Mar. 24, 2014.
International Search Report for PCT/EP2012/003247 dated Oct. 18, 2012.
English-translation of International Preliminary Report on Patentability for PCT/EP2012/003244 dated Feb. 4, 2014.
International Search Report for PCT/EP2012/003244 dated Oct. 18, 2012.
English-translation of International Preliminary Report on Patentability for PCT/EP2012/003253 dated Feb. 4, 2014.
International Search Report for PCT/EP2012/003253 dated Oct. 8, 2012.
English-translation of International Preliminary Report on Patentability for PCT/EP2012/003252 dated Feb. 4, 2014.
International Search Report for PCT/EP2012/003252 dated Oct. 8, 2012.
English-translation of International Preliminary Report on Patentability for PCT/EP2012/003245 dated Feb. 21, 2014.
International Search Report for PCT/EP2012/003245 dated Oct. 5, 2012.
International Search Report for PCT/EP2012/003251 dated Oct. 10, 2012.
Translation of International Preliminary Report on Patentability for PCT/EP2012/003251 dated Feb. 4, 2014.
International Search Report for PCT/EP2012/003250 dated Oct. 5, 2012.
Translation of International Preliminary Report on Patentability for PCT/EP2012/003250 dated Feb. 4, 2014.
International Search Report for PCT/EP2012/003249 dated Oct. 5, 2012.
Translation of International Preliminary Report on Patentability for PCT/EP2012/003249 dated Feb. 4, 2014.
International Search Report for PCT/EP2012/004827 dated Jan. 7, 2014.

(56) References Cited

OTHER PUBLICATIONS

Translation of International Preliminary Report on Patentability for PCT/EP2012/004827 dated Jan. 7, 2014.
USPTO Final Rejection for US U.S. Appl. No. 13/321,178, dated Dec. 4, 2013.
USPTO Non-Final Rejection for U.S. Appl. No. 13/321,178, dated Apr. 30, 2013.
USPTO Non-Final Rejection for U.S. Appl. No. 13/321,178, dated May 6, 2014.
USPTO Requirement for Restriction/Election for U.S. Appl. No. 13/321,178, dated Jan. 10, 2013.
USPTO Final Rejection for U.S. Appl. No. 13/321,199, dated Mar. 19, 2015.
USPTO Final Rejection for U.S. Appl. No. 13/321,199, dated Dec. 24, 2013.
USPTO Non-Final Rejection for U.S. Appl. No. 13/321,199, dated Apr. 22, 2013.
USPTO Non-Final Rejection for U.S. Appl. No. 13/321,199, dated Aug. 18, 2015.
USPTO Non-Final Rejection for U.S. Appl. No. 13/321,199, dated Sep. 5, 2014.
USPTO Requirement for Restriction/Election for U.S. Appl. No. 13/321,199, dated Nov. 7, 2012.
USPTO Non-Final Rejection for U.S. Appl. No. 14/237,024, dated Mar. 4, 2015.
USPTO Requirement for Restriction/Election for U.S. Appl. No. 14/237,027, dated Jan. 28, 2015.
USPTO Final Rejection for U.S. Appl. No. 14/237,042, dated Jul. 8, 2015.
USPTO Non-Final Rejection for U.S. Appl. No. 14/237,042, dated Dec. 17, 2014.
USPTO Non-Final Rejection for U.S. Appl. No. 14/237,042, dated Feb. 25, 2016.
USPTO Notice of Allowance for U.S. Appl. No. 14/237,042, dated Oct. 7, 2016.
USPTO Non-Final Rejection for U.S. Appl. No. 14/237,034, dated Mar. 6, 2015.
USPTO Notice of Allowance for U.S. Appl. No. 14/237,034, dated Feb. 10, 2016.
USPTO Final Rejection for U.S. Appl. No. 14/237,053, dated Sep. 8, 2015.
USPTO Non-Final Rejection for U.S. Appl. No. 14/237,053, dated May 7, 2015.
USPTO Ex Parte Quayle Action for U.S. Appl. No. 14/237,071, dated Jun. 24, 2015.
USPTO Requirement for Restriction/Election for U.S. Appl. No. 14/237,071, dated Jan. 28, 2015.
USPTO Non-Final Rejection for U.S. Appl. No. 14/237,076, dated Sep. 9, 2015.

\* cited by examiner

USE OF ISOSORBIDE MONOESTERS AS ANTIMICROBIAL ACTIVE SUBSTANCES

The present invention relates to the use of isosorbide monoesters as antimicrobially active compounds.

In industry, preservatives or biocides are used to protect products such as, for example, cosmetic, dermatological or pharmaceutical compositions, crop protection formulations, washing or cleaning compositions or paints or coatings against microbial attack. Numerous preservatives or biocides which can be used for this purpose are known. For this purpose, use may be made, for example, of preservatives from Annex V of the EU Cosmetics Directive or biocides of the EU Biocides Directive.

However, many preservatives have the disadvantage that, frequently, their preparation is expensive and based on synthetic raw materials. In addition, their preserving action frequently requires improvement, with high use concentrations being required for satisfactory preservation.

Accordingly, it was an object of the present invention to provide antimicrobially active compounds which have an advantageous preservation performance and which are furthermore distinguished by the advantage that they are based on renewable raw materials.

Surprisingly, it has now been found that this object is achieved by compounds of the formula (I)

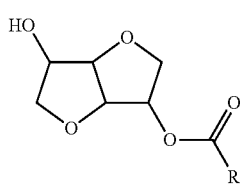

(I)

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms.

Accordingly, the invention provides the use of one or more compounds of the formula (I)

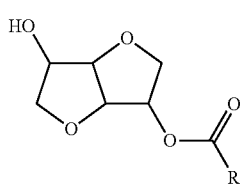

(I)

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms as antimicrobially active compound.

The compounds of the formula (I) have very good preservative performance and are preferably suitable for use as fungicides. Moreover, they are based on renewable raw materials.

Compared to the use of organic acids as preservatives, the compounds of the formula (I) additionally have the advantage of being active over a broader pH range. Whereas organic acids frequently only have good activity in the pH range from 3.5 to 6, the compounds of the formula (I) can also be employed advantageously at higher pH.

Compositions which are based at least in part on renewable raw materials and can be used as preservatives are already known.

DE 10 2009 022 444 (Clariant) describes liquid compositions comprising sorbitan monocaprylate and antimicrobially active compounds such as, for example, specific organic acids and their salts, specific formaldehyde donors, specific isothiazolinones, specific paraben esters and their salts and specific pyridones and their salts, and also their use for preserving cosmetic, dermatological or pharmaceutical products.

DE 10 2009 022 445 (Clariant) discloses liquid compositions comprising sorbitan monocaprylate and alcohol and their use for preserving cosmetic, dermatological or pharmaceutical products.

JP 8187070 (A) (Lion) discloses a mixture of fatty acid monoesters of $C_8$-$C_{18}$ fatty acids and at least one polyol selected from sorbitol, 1,5-sorbitan, 1,4-sorbitan and isosorbide and fatty acid diesters of these fatty acids and polyols in a weight ratio of monoester:diester of 33:7 to 9:1 as antimicrobially active compound against bacteria for food or beverages.

Compounds of the formula (I) can be prepared, for example, by methods familiar to the person skilled in the art. For example, the compounds of the formula (I) can be prepared by esterification of isosorbide by customary methods known to the person skilled in the art, with both isosorbide for its part and also the acid components used for esterification once more being commercially available.

The one or more compounds of the formula (I) are preferably used as fungicide. In the context of the present application, this means that the one or more compounds of the formula (I) may preferably be employed as antimicrobially active compound against yeasts and fungi. With particular preference, the one or more compounds of the formula (I) are employed as antimicrobially active compound against fungi.

Preferably, the radical R in the one or more compounds of the formula (I) is a straight-chain saturated alkyl radical having 7 to 9 carbon atoms.

Particularly preferably, the radical R in the one or more compounds of the formula (I) is a straight-chain saturated alkyl radical having 7 carbon atoms.

According to the invention, the one or more compounds of the formula (I) can be used on their own or in compositions comprising one or more other substances as antimicrobially active compounds. Hereinbelow, these compositions are referred to as "compositions A".

In a preferred embodiment of the invention, the compositions A comprise one or more compounds of the formula (I) and additionally one or more other substances selected from the group consisting of sorbitol, sorbitol esters (sorbitol esters can be mono-, di-, tri-, tetra-, penta- and/or hexaesters), sorbitan, sorbitan esters (sorbitan esters can be mono-, di-, tri- and/or tetraesters), isosorbide, isosorbide diesters and carboxylic acids. "Sorbitan" can be, for example, 1,4- or 1,5-sorbitan. Both the carboxylic acids themselves and the carboxylic acids on which the acid components of the esters mentioned are based correspond to the formula RCOOH in which R has the meaning given for formula (I) and is preferably a straight-chain saturated alkyl radical having 7 carbon atoms, i.e. the carboxylic acid RCOOH is preferably caprylic acid.

In a particularly preferred embodiment of the invention, the compositions A comprise one or more compounds of the formula (I) and additionally I) isosorbide and II) one or more isosorbide diesters of the formula (II)

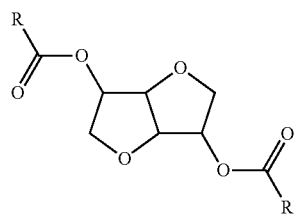

where R has the meaning given above for formula (I) and where the isosorbide diester is preferably isosorbide dicaprylate.

From among these compositions, the compositions A just mentioned again preferably comprise one or more compounds of the formula (I) and additionally I) from 0.05 to 0,7, preferably from 0.1 to 0.7 and particularly preferably from 0.2 to 0.5 part by weight of isosorbide and II) from 0.1 to 1.0, preferably from 0.2 to 1.0 and particularly preferably from 0.4 to 0.8 part by weight of the one or more isosorbide diesters of the formula (II), where the isosorbide diester is preferably isosorbide dicaprylate, in each case based on 1.0 part by weight of the one or more compounds of the formula (I) and preferably based on 1.0 part by weight of isosorbide monocaprylate.

In a once again preferred embodiment of the invention, the compositions A just mentioned comprise either no carboxylic acid RCOOH or up to 0.1, preferably 0.001 to 0.05 and particularly preferably 0.002 to 0.01 part by weight of carboxylic acid RCOOH, where R has the meaning given above for formula (I) and where the carboxylic acid is preferably caprylic acid, based on 1.0 part by weight of the one or more compounds of the formula (I) and preferably based on 1.0 part by weight of isosorbide monocaprylate.

In a further particularly preferred embodiment of the invention, the compositions A comprise one or more compounds of the formula (I) and one or more sorbitan esters of sorbitan and carboxylic acids $R^aCOOH$, preferably selected from sorbitan esters from 1,4- and/or 1,5-sorbitan and carboxylic acids $R^aCOOH$, where $R^a$ is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and where the weight ratio of the one or more compounds of the formula (I) to the one or more sorbitan esters just mentioned is from 70:30 to 100:0, preferably from 80:20 to 100:0, particularly preferably from 90:10 to 100:0 and especially preferably from 95:5 to 100:0. The stated weight ratio of "100:0" means that in this particularly preferred embodiment of the invention, the compositions A just mentioned do not need to comprise any sorbitan ester.

From among the compositions A just mentioned, preference is given to those in which the one or more sorbitan esters of sorbitan and carboxylic acids $R^aCOOH$ are selected from sorbitan esters of sorbitan and caprylic acid and are preferably selected from sorbitan esters of 1,4- and/or 1,5-sorbitan and caprylic acid and the sorbitan ester is particularly preferably sorbitan monocaprylate.

In these compositions A, the hydroxyl value of the mixture of the one or more compounds of the formula (I) and the one or more (if present) sorbitan esters of sorbitan and carboxylic acids $R^aCOOH$ is preferably smaller than or equal to 320, particularly preferably smaller than or equal to 285, especially preferably smaller than or equal to 245 and most preferably smaller than or equal to 225.

In a further particularly preferred embodiment of the invention, the hydroxyl value of the mixture of the one or more compounds of the formula (I) and the one or more compounds selected from the group consisting of sorbitol, sorbitol esters, sorbitan, sorbitan esters, isosorbide, isosorbide diesters and carboxylic acids in the compositions A is smaller than or equal to 320, preferably smaller than or equal to 285, particularly preferably smaller than or equal to 245 and especially preferably smaller than or equal to 225.

In a further particularly preferred embodiment of the invention, the compositions A do not comprise any compounds selected from sorbitol and sorbitol esters.

In a further particularly preferred embodiment of the invention, the compositions A do not comprise any compounds selected from sorbitan and sorbitan esters.

If the compositions A comprise one or more compounds selected from the acid component sorbitol and sorbitol esters (where the carboxylic acid on which of these esters is based is preferably caprylic acid), these compounds together are preferably present in the compositions A in an amount smaller than or equal to 5.0% by weight, particularly preferably in an amount smaller than or equal to 3.0% by weight, especially preferably in an amount smaller than or equal to 1.0% by weight and most preferably in an amount smaller than or equal to 0.5% by weight, the stated % by weight in each case being based on the total weight of the finished compositions A.

If the compositions A comprise one or more compounds selected from sorbitan and sorbitan esters (where the carboxylic acid on which the acid component of these esters is based is preferably caprylic acid), these compounds together are preferably present in the compositions A in an amount smaller than or equal to 20.0% by weight, particularly preferably in an amount smaller than or equal to 10.0% by weight, especially preferably in an amount smaller than or equal to 5.0% by weight and most preferably in an amount smaller than or equal to 1.0% by weight, the stated % by weight in each case being based on the total weight of the finished compositions A.

In a further particularly preferred embodiment of the invention, the compositions A comprise the one or more compounds of the formula (I) in amounts of at least 30% by weight, preferably in amounts of at least 50% by weight and particularly preferably in amounts of at least 60% by weight, in each case based on the total weight of the finished compositions A.

The hydroxyl value of a substance is to be understood as meaning the amount of KOH in mg equivalent to the amount of acetic acid bound during the acetylation of 1 g of substance.

Suitable determination methods for determining the hydroxyl value are, for example, DGF C-v 17 a (53), Ph. Eur. 2.5.3 Method A and DIN 53240.

In the context of the present invention, the hydroxyl values are determined analogously to DIN 53240-2. Here, the following procedure is adopted: 1 g, accurate to 0.1 mg, of the homogenized sample to be measured is weighed out. 20.00 ml of acetylation mixture (acetylation mixture: 50 ml of acetic anhydride are stirred into 1 liter of pyridine) are added. The sample is dissolved completely in the acetylation mixture, if required with stirring and heating. 5 ml of catalyst solution (catalyst solution: 2 g of 4-dimethylaminopyridine are dissolved in 100 ml of pyridine) are added. The reaction vessel is closed and placed into the water bath, preheated to 55° C., for 10 minutes, with mixing. 10 ml of fully deionized water are then added to the reaction solution, the reaction vessel is closed again and the mixture is once more allowed to react in the water bath with shaking for 10 minutes. The sample is then cooled to room temperature (25° C.). 50 ml of 2-propanol and 2 drops of phenolphthalein are then added. This solution is titrated with aqueous sodium hydroxide solution (aqueous sodium hydroxide solution c=0.5 mol/l) (Va). Under identical conditions, but without any sample added, the efficacy of the acetylation mixture is determined (Vb).

From the aqueous sodium hydroxide solution consumed in the determination of the efficacy and the titration of the sample, the hydroxyl value (OHV) is calculated using the following formula:

$$OHV = \frac{(Vb - Va) \cdot c \cdot t \cdot M}{E}$$

OHV=hydroxyl value in mg KOH/g substance
Va=aqueous sodium hydroxide solution consumed in ml during the titration of the sample
Vb=aqueous sodium hydroxide solution consumed in ml during the titration of efficacy
c=molar concentration of the aqueous sodium hydroxide solution in mol/l
t=titer of the aqueous sodium hydroxide solution
M=molar mass of KOH=56.11 g/mol
E=sample weighed out in g
(Vb−Va) is the amount of aqueous sodium hydroxide solution used in ml, which is equivalent to the amount of acetic acid bound during the above-described acetylation of the sample to be measured.

Hereinbelow, the method just described for determining the hydroxyl value is referred to as "method OHV-A".

Preferably, the use according to the invention is in cosmetic, dermatological or pharmaceutical compositions, in crop protection formulations, in washing or cleaning compositions or in paints or coatings. The crop protection compositions preferably comprise one or more pesticides.

The cosmetic, dermatological or pharmaceutical compositions, the crop protection formulations, the washing or cleaning compositions or the paints or coatings comprise the one or more compounds of the formula (I) preferably in amounts of from 0.01 to 10.0% by weight, particularly preferably in amounts of from 0.1 to 5.0% by weight and especially preferably in amounts of from 0.2 to 3.0% by weight, in each case based on the total weight of the finished cosmetic, dermatological or pharmaceutical compositions, crop protection formulations, washing or cleaning compositions or paints or coatings.

The cosmetic, dermatological or pharmaceutical compositions, the crop protection formulations, the washing or cleaning compositions or the paints or coatings have viscosities preferably in the range from 50 to 200 000 mPa·s, particularly preferably in the range from 500 to 100 000 mPa·s, especially preferably in the range from 2 000 to 50 000 mPa·s and most preferably in the range from 5 000 to 30 000 mPa·s (20° C., Brookfield RVT, RV spindle set at 20 revolutions per minute).

The cosmetic, dermatological or pharmaceutical compositions are preferably present in the form of fluids, gels, foams, sprays, lotions or creams.

The cosmetic, dermatological or pharmaceutical compositions are preferably compositions for treating Athlete's foot or antidandruff compositions. In these cases, the use according to the invention is as fungicide for Athlete's foot and for dandruff.

The cosmetic, dermatological or pharmaceutical compositions, the crop protection formulations, the washing or cleaning compositions or the paints or coatings are preferably formulated on an aqueous or aqueous-alcoholic basis or are present as emulsions or dispersions. Particularly preferably, they are present as emulsions, and especially preferably they are present as oil-in-water emulsions.

As further auxiliaries and additives, the cosmetic, dermatological or pharmaceutical compositions, the crop protection formulations, the washing or cleaning compositions or the paints or coatings may comprise all substances customarily used for the application in question, for example oils, waxes, emulsifiers, co-emulsifiers, dispersants, surfactants, defoamers, solubilizers, electrolytes, hydroxy acids, stabilizers, polymers, film formers, thickeners, gelling agents, superfattening agents, refattening agents, further antimicrobially active compounds, biogenic active compounds, adstringents, active compounds, deodorizing compounds, sun protection filters, antioxidants, oxidants, moisturizers, solvents, colorants, pigments, pearlizing agents, fragrances, opacifiers and/or silicones.

The cosmetic, dermatological or pharmaceutical compositions, the crop protection formulations, the washing or cleaning compositions or the paints or coatings have a pH of preferably from 2 to 11, particularly preferably from 4.5 to 8.5 and especially preferably from 5.5 to 6.5.

The examples and applications which follow are intended to illustrate the invention in more detail, without limiting it. All percentages are % by weight, unless explicitly stated otherwise.

EXPERIMENTAL EXAMPLES

A) Preparation of Isosorbide Caprylate

In a stirred apparatus with distillation head, 190.0 g (1.3 mol) of isosorbide ("Sorbon" from Ecogreen Oleochemicals) and 187.5 g (1.3 mol) of octanoic acid (caprylic acid) are initially charged at 80° C. together with 0.38 g of aqueous sodium hydroxide solution (18% by weight strength, aqueous) as catalyst. With stirring and under a flow of nitrogen (10-12 liters per hour), the reaction mixture is initially heated to 180° C., where the water of reaction begins to distill off. The reaction is then heated to 190° C. over a period of 1 hour and to 210° C. over a further 2 hours. After 210° C. is reached, the esterification is continued until an acid value of <1 mg KOH/g is reached. This gives 345.7 g of amber isosorbide caprylate (97% of theory). The pH (5% by weight in ethanol/water 1:1) is 5.9. The pH was measured according to DIN EN 1262.

Further analytical characteristics of the isosorbide caprylate:
Acid value: 0.9 mg KOH/g, measured according to DIN EN ISO 2114
Hydroxyl value: 206 mg KOH/g, measured analogously to DIN 53240-2 according to method OHV-A Saponification value: 204 mg KOH/g, measured according to DIN EN ISO 3681

The isosorbide caprylate has the following composition:

| Substance | % by weight |
|---|---|
| caprylic acid | 0.4 |
| isosorbide | 18.1 |
| isosorbide monocaprylate | 50.9 |
| isosorbide dicaprylate | 30.6 |

Hereinbelow, this composition is referred to as "isosorbide caprylate 1".

B) Determination of the Antimicrobial Efficacy of Isosorbide Caprylate 1

Below, the antimicrobial efficacy of isosorbide caprylate 1 in butyl polyglycol against bacteria, fungi and yeasts is examined. For the tests with bacteria, isosorbide caprylate 1 was diluted with butyl polyglycol and then, at 50° C., added to liquid CASO agar (casein-peptone agar) buffered to pH 7 (+1-0.2) in various concentrations (hereinbelow referred to as compositions B1, B2, etc.). For the tests with fungi and yeasts, isosorbide caprylate 1 was diluted with butyl polyglycol and then added to liquid Sabouraud 4% dextrose agar buffered to pH 5.6 (+1-0.2) in various concentrations (hereinbelow referred to as compositions PH1, PH2, etc.). The compositions B1, B2, etc. and PH1, PH2 etc. were each poured into Petri dishes and each inoculated with identical amounts of bacteria, fungi and yeasts. The minimum inhibitory concentration (MIC) is the concentration at which inhibition of the growth of the bacteria, fungi and yeasts in the compositions B1, B2, etc. and PH1, PH2, etc. occurs.

The values determined for the minimum inhibitory concentrations of isosorbide caprylate 1, stated in Table 1 below, have already been corrected for the dilution effect of the butyl polyglycol.

TABLE 1

Minimum inhibitory concentrations (MIC) of isosorbide caprylate 1

| Bacteria (B), fungi (F) or yeasts (Y) examined | MIC of isosorbide caprylate 1 [ppm] |
|---|---|
| Staphylococcus aureus (B) | 2500 |
| Pseudomonas aeruginosa (B) | 10000 |
| Escherichia coli (B) | 7500 |
| Enterobacter aerogenes (B) | 10000 |
| Klebsiella pneumoniae (B) | 10000 |
| Proteus vulgaris (B) | 5000 |
| Pseudomonas oleovorans (B) | 10000 |
| Citrobacter freundii (B) | 10000 |
| Candida albicans (Y) | 600 |
| Aspergillus brasiliensis (F) | 800 |
| Penicillium minioluteum (F) | 600 |
| Aspergillus terreus (F) | 600 |
| Fusarium solani (F) | 600 |
| Penicillium funicolosium (F) | 400 |

The results listed in Table 1 show that isosorbide caprylate 1 is antimicrobially active, in particular against the yeast *Candida albicans* and the fungi tested.

C) Antimicrobial Activity of the Constituents of Isosorbide Caprylate 1

Caprylic acid is antimicrobially effective. However, since in the composition "isosorbide caprylate 1" caprylic acid is present in an amount of only 0.4% by weight, its antimicrobial efficacy in this composition is so low that it can be neglected. In addition, caprylic acid has no antimicrobial activity at a pH of 6 or above.

Analogously to the determination of the antimicrobial activity of isosorbide caprylate 1, the antimicrobial activity firstly of a mixture comprising 89.6% by weight of isosorbide dicaprylate and 9.4% by weight of isosorbide monocaprylate (remainder: 1% by weight) (hereinbelow referred to as "isosorbide dicaprylate") and, secondly, pure isosorbide was determined in further test series. The results are shown in Table 2:

TABLE 2

Minimum inhibitory concentrations (MIC) of isosorbide dicaprylate and isosorbide

| Bacteria (B), fungi (F) or yeasts (Y) examined | MIC of isosorbide dicaprylate [ppm] | MIC of isosorbide [ppm] |
|---|---|---|
| Staphylococcus aureus (B) | 10000 | 10000 |
| Pseudomonas aeruginosa (B) | 10000 | 10000 |
| Escherichia coli (B) | 10000 | 10000 |
| Enterobacter aerogenes (B) | 10000 | 10000 |
| Klebsiella pneumoniae (B) | 10000 | 10000 |
| Proteus vulgaris (B) | 10000 | 10000 |
| Pseudomonas oleovorans (B) | 10000 | 10000 |
| Citrobacter freundii (B) | 10000 | 10000 |
| Candida albicans (Y) | 10000 | 10000 |
| Aspergillus brasiliensis (F) | 10000 | 10000 |
| Penicillium minioluteum (F) | 10000 | 10000 |
| Aspergillus terreus (F) | 10000 | 10000 |
| Fusarium solani (F) | 5000 | 10000 |
| Penicillium funicolosium (F) | 5000 | 10000 |

As shown by the results of Table 2, neither isosorbide nor isosorbide dicaprylate is antimicrobially active.

From the lack of antimicrobial activity of the compounds caprylic acid, isosorbide and isosorbide dicaprylate present in the composition isosorbide caprylate 1 on the one hand and from the antimicrobial activity of the composition "isosorbide caprylate 1" evident from the results of Table 1 on the other hand, it can be concluded that the compound isosorbide monocaprylate likewise present in the composition isosorbide caprylate 1 has significant antimicrobial activity, in particular as fungicide against fungi and yeasts.

For this reason, it is also thought that the low activity of the composition isosorbide dicaprylate with respect to the fungi *Fusarium solani* and *Penicillium funicolosium* is due to the compound isosorbide monocaprylate present therein.

D) Use Examples

The use according to the invention can take place, for example, in the following formulations.

Formulation Example 1: Revitalising Moisturizing Cream

| Phase | Ingredient | % by weight |
|---|---|---|
| A | Hostacerin ® SFO sunflower seed oil sorbitol esters | 2.0 |
| | Velsan ® CCT caprylic/capric triglyceride | 4.5 |
| | Cetiol ® OE dicaprylyl ether | 4.5 |

-continued

| Phase | Ingredient | % by weight |
|---|---|---|
| | Lanette ® 22 | 4.0 |
| | behenyl alcohol | |
| | Lanette ® 18 | 4.0 |
| | stearyl alcohol | |
| | Fucogel ® 1000 | 1.0 |
| | biosaccharide gum-1 | |
| B | Coenzyme ® Q 10 | 0.1 |
| | ubiquinone | |
| C | water | ad 100 |
| | glycerol | 10.0 |
| | Hostaphat ® CK 100 | 0.6 |
| | potassium cetyl phosphate | |
| D | phenoxyethanol | 1.0 |
| | isosorbide caprylate 1 | 1.0 |
| E | NaOH (10% by weight in water) | q.s. |

Preparation:
I   The components of A are mixed and the mixture is heated to 80° C.
II  The components of C are mixed and the mixture is heated to 80° C.
III B is added to I.
IV  II is added to III and the mixture is stirred until it has cooled to room temperature.
V   D is added to IV.
VI  The pH is adjusted to 5.5 using E.

Formulation Example 2

| Phase | Ingredient | % by weight |
|---|---|---|
| A | Hostacerin ® EWO | 16.0 |
| | polyglyceryl 2-sesquiisostearate (and) cera alba (and) carnauba wax (and) ethylhexyl stearate (and) magnesium stearate (and) aluminum stearate | |
| | isopropyl palmitate | 10.0 |
| | avocado oil | 2.0 |
| | Velsan ® CCT | 2.5 |
| | caprylic/capric triglyceride | |
| B | Octopirox ® | 0.05 |
| | piroctone olamine | |
| | propylene glycol | 1.0 |
| C | water | ad 100 |
| | glycerol | 4.0 |
| | magnesium sulfate * 7 H$_2$O | 0.7 |
| | allantoin | 0.5 |
| D | tocopheryl acetate | 0.5 |
| | Rosmarinus officinalis (rosemary) leaf oil | 0.1 |
| | urea | 10.0 |
| | isosorbide caprylate 1 | 1.0 |
| | phenoxyethanol | 0.8 |

Preparation:
I   The components of A are mixed and the mixture is heated to 80° C.
II  The components of B are mixed until all substances have been dissolved (if required with gentle heating).
III II is added to I.
IV  The components of C are mixed and the mixture is heated to 50° C.
V   IV is stirred into I at high speed until the mixture has cooled to 35° C.
VI  D is added to V at 35° C.

Formulation Examples 3 and 4: Crop Protection Formulations

| | Formulation No. | |
|---|---|---|
| | 3 | 4 |
| Ingredient | Amount of the respective ingredient [% by weight] | |
| atrazine | 43.6 | 43.6 |
| Dispersogen ® PSL 100 | — | 1.7 |
| Genapol ® LSS | — | 1.6 |
| Dispersogen ® LFS | 2.1 | — |
| propylene glycol | 4.3 | 4.3 |
| Defoamer ® SE 57 | 0.6 | 0.6 |
| Kelzan ® S (2% by weight in water) | 7.3 | 7.3 |
| isosorbide caprylate 1 | 0.3 | 0.2 |
| benzyl alcohol | 1.0 | 1.0 |
| Water | ad 100 | ad 100 |

Preparation:
The active compound is pre-dispersed with the other ingredients (except for the Kelzan ® S solution) and then subjected to fine grinding until the mean particle size is < 2 micrometers. The Kelzan ® S solution is then stirred in.

Formulation Example 5: Dishwashing Liquids

| Ingredient | % by weight |
|---|---|
| Hostapur ® SAS 60 | 40.0 |
| (alkanesulfonate, 60% by weight in water) | |
| Hostapur ® OS liquid | 11.0 |
| (sodium C14-16 alkyl sulfonate, 40% by weight in water) | |
| Genaminox ® LA | 3.0 |
| (dimethyllauramine oxide, 30% by weight in water) | |
| Genagen ® CAB | 3.0 |
| (cocoamidopropyl betaine, 30% by weight in water) | |
| isosorbide caprylate 1 | 0.8 |
| benzyl alcohol | 0.8 |
| Water | ad 100 |

Formulation Example 6: Surface Cleaners (All-Purpose Cleaners)

| Ingredient | % by weight |
|---|---|
| Hostapur ® SAS 60 | 5.0 |
| (alkanesulfonate, 60% by weight in water) | |
| Genapol ® UD 080 | 2.0 |
| (undecanol + 8 EO) | |
| Genaminox ® LA | 2.0 |
| (dimethyllauramine oxide, 30% by weight in water) | |
| methylisothiazolinone | 0.01 |
| isosorbide caprylate 1 | 1.0 |
| Water | ad 100 |

Preparation of Formulation Examples 5 and 6

Half of the amount of water is initially charged and the components are stirred in in the same order as listed in the tables given for formulation examples 5 and 6. The remaining water is then added. This gives clear aqueous compositions.

The invention claimed is:
1. A method for destroying fungus or inhibiting fungal growth, comprising the step of contacting at least one fungi with a composition comprising at least one compound of the formula (I)

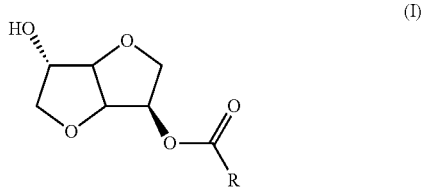

in which
R is a straight-chain or branched saturated alkyl group having 5 to 11 carbon atoms or a straight-chain or branched mono- or polyunsaturated alkenyl group having 5 to 11 carbon atoms.
2. The method as claimed in claim 1, wherein the radical R in formula (I) is a straight-chain saturated alkyl radical having 7 to 9 carbon atoms.
3. The method as claimed in claim 2, wherein the radical R in formula (I) is a straight-chain saturated alkyl radical having 7 carbon atoms.
4. The method as claimed in claim 1, wherein the composition further comprises at least one substance selected from the group consisting of sorbitol, sorbitol esters, sorbitan, sorbitan esters, isosorbide, isosorbide diesters and carboxylic acids.
5. The method as claimed in claim 4, wherein the composition further comprises
I) isosorbide and
II) at least one isosorbide diester of the formula (II)

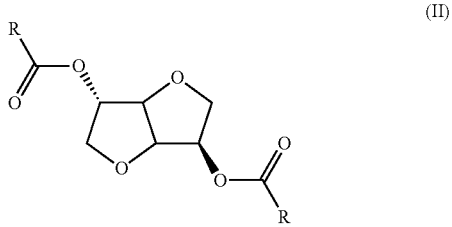

where R is a straight-chain or branched saturated alkyl group having 5 to 11 carbon atoms or a straight-chain or branched mono- or polyunsaturated alkenyl group having 5 to 11 carbon atoms.
6. The method as claimed in claim 1, wherein the composition further comprises I) from 0.05 to 0.7 part by weight of isosorbide and
II) from 0.1 to 1.0 part by weight of the one or more isosorbide diesters of the formula (II),
in each case based on 1.0 part by weight of the at least one compound of the formula (I).
7. The method as claimed in claim 4, wherein the composition further comprises at least one sorbitan ester of sorbitan and carboxylic acid $R^a$COOH, where $R^a$ is a straight-chain or branched saturated alkyl group having 5 to 11 carbon atoms or a straight-chain or branched mono- or polyunsaturated alkenyl group having 5 to 11 carbon atoms, and where the weight ratio of the at least one compound of the formula (I) to the at least one sorbitan ester is from 70:30 to 100:0.
8. The method as claimed in claim 7, wherein the carboxylic acid $R^a$COOH is selected from the group consisting of caprylic acid.
9. The method as claimed in claim 4, wherein the hydroxyl value of the mixture of the at least one compound of the formula (I) and the at least one compound selected from the group consisting of sorbitol, sorbitol esters, sorbitan, sorbitan esters, isosorbide, isosorbide diesters and carboxylic acids in the composition is less than or equal to 320.
10. The method as claimed in claim 4, wherein the composition comprises the at least one compound of the formula (I) in an amount of at least 30% by weight, in each case based on the total weight of the finished composition.
11. The method as claimed in claim 1 for preventing fungal growth in a cosmetic, dermatological or pharmaceutical composition, in a crop protection formulation, in a washing or cleaning composition or in a paint or coating.
12. The method as claimed in claim 11, wherein the cosmetic, dermatological or pharmaceutical composition, the crop protection formulation, the washing or cleaning composition or the paint or coating comprise the at least one compound of the formula (I) in an amount of from 0.01 to 10.0% by weight, in each case based on the total weight of the finished cosmetic, dermatological or pharmaceutical composition, crop protection formulation, washing or cleaning composition or paint or coating.
13. The method as claimed in claim 11, wherein the cosmetic, dermatological or pharmaceutical composition, the crop protection formulation, the washing or cleaning composition or the paint or coating is formulated on an aqueous or aqueous-alcoholic basis or are present as emulsion or dispersion.
14. The method as claimed in claim 11, wherein the cosmetic, dermatological or pharmaceutical composition, the crop protection formulation, the washing or cleaning composition or the paint or coating has a pH of from 2 to 11.
15. The method as claimed in claim 11, wherein the cosmetic, dermatological or pharmaceutical composition, the crop protection formulation, the washing or cleaning composition or the paint or coating is formulated as an emulsion.

* * * * *